Figure 1:
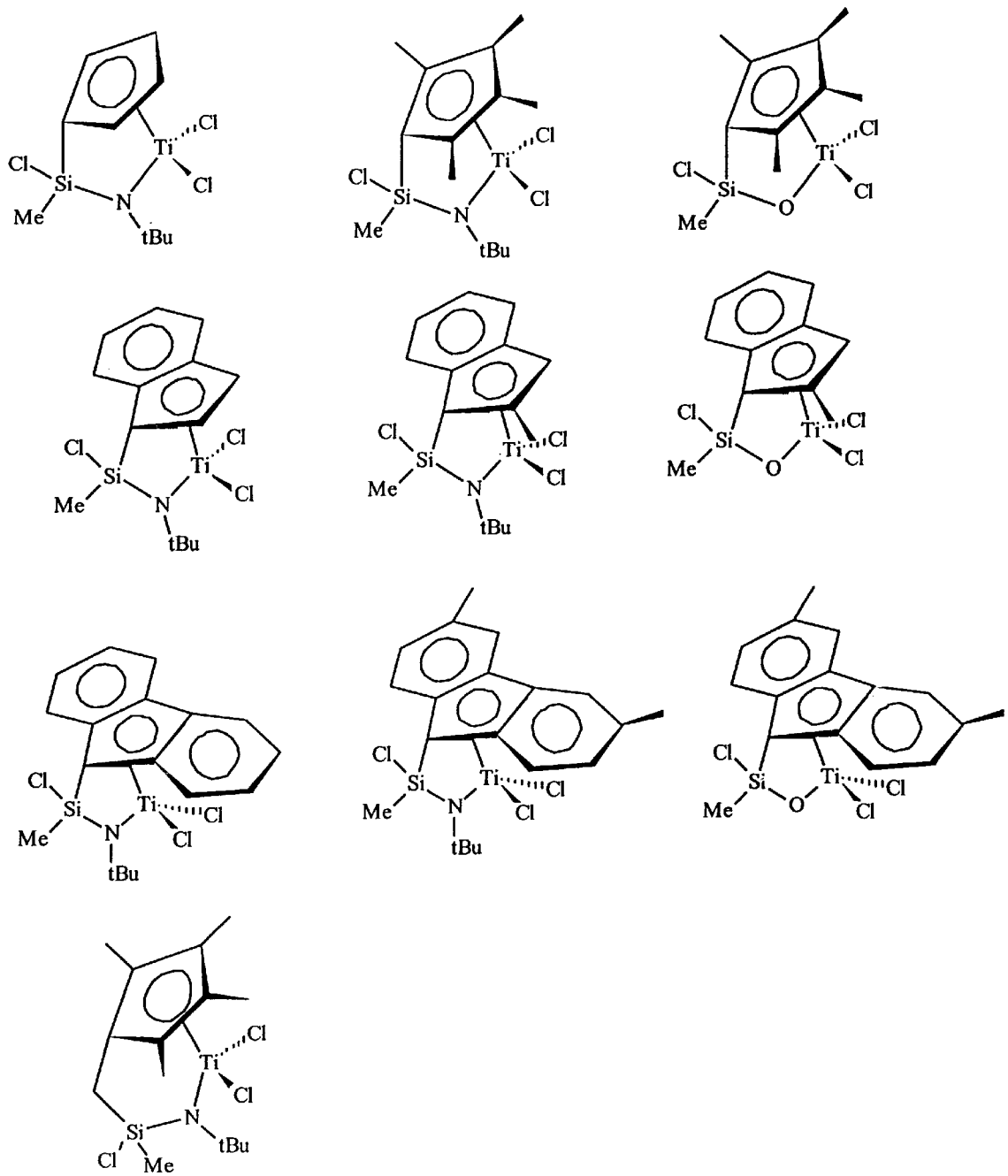

United States Patent [19]
Royo et al.

[11] Patent Number: 5,977,392
[45] Date of Patent: Nov. 2, 1999

[54] ORGANOMETALLIC CATALYSTS FOR THE POLYMERIZATION AND COPOLYMERIZATION OF ALPHA-OLEFINS

[75] Inventors: Jose Sancho Royo; Antonio Muñoz-Escalona Lafuente; Begoña Peña García; Carlos Martin Marcos, all of Madrid, Spain

[73] Assignee: Respol Quimica S.A., Madrid, Spain

[21] Appl. No.: 08/961,349

[22] Filed: Oct. 30, 1997

[30] Foreign Application Priority Data

Oct. 30, 1996 [ES] Spain ................ 9602302

[51] Int. Cl.⁶ .............. C07F 17/00; C07F 7/00; C08F 4/643; B01J 31/00
[52] U.S. Cl. ............ 556/11; 502/103; 502/117; 502/120; 502/152; 526/127; 526/130; 526/134; 526/160; 526/943; 534/11; 534/15; 556/7; 556/8; 556/20; 556/21; 556/43; 556/46; 556/52; 556/58; 556/136; 556/137; 556/140; 556/146
[58] Field of Search .................. 556/7, 8, 11, 20, 556/21, 43, 46, 52, 58, 136, 137, 140, 146; 534/11, 15; 502/108, 117, 120, 152; 526/127, 130, 134, 160, 943

[56] References Cited

U.S. PATENT DOCUMENTS

| | | | |
|---|---|---|---|
| 3,184,416 | 5/1965 | Mottus | 252/429 |
| 3,440,237 | 4/1969 | Mottus | 260/94.9 |
| 4,542,199 | 9/1985 | Kaminsky et al. | 526/160 |
| 4,939,217 | 7/1990 | Stricklen | 526/114 |
| 5,057,475 | 10/1991 | Canich et al. | 502/104 |
| 5,064,797 | 11/1991 | Stricklen | 502/111 |
| 5,688,880 | 11/1997 | Spencer et al. | 526/127 |

FOREIGN PATENT DOCUMENTS

| | | |
|---|---|---|
| 0 277 004 | 8/1988 | European Pat. Off. |
| 0 293 815 | 12/1988 | European Pat. Off. |
| 0 323 716 | 7/1989 | European Pat. Off. |
| 0 336 593 | 10/1989 | European Pat. Off. |
| 0 361 866 | 4/1990 | European Pat. Off. |
| 0 367 503 | 5/1990 | European Pat. Off. |
| 0 368 644 | 5/1990 | European Pat. Off. |
| 0 416 815 | 3/1991 | European Pat. Off. |
| 0 420 436 | 4/1991 | European Pat. Off. |
| 0 426 637 | 5/1991 | European Pat. Off. |
| 0 633 272 | 1/1995 | European Pat. Off. |
| 0 668 295 | 8/1995 | European Pat. Off. |
| 0 757 992 | 8/1996 | European Pat. Off. |
| 1 022 382 | 5/1963 | Germany. |
| WO 92/05203 | 4/1992 | WIPO. |
| WO 94/03506 | 2/1994 | WIPO. |
| WO 94/07928 | 4/1994 | WIPO. |

OTHER PUBLICATIONS

Spence et al., Organometallics, vol. 14, pp. 4617–4624, 1995.

Okuda et al., Chem. Ber., vol. 129, pp. 1429–1431, 1996.

Ciruelos et al., Organometallics, vol. 14, pp. 177–185, 1995.

J. Cihlar, et al., Influence of Water on Ethylene Polymerization Catalyzed by Titanocene Systems, *Macromol. Chem.*, vol. 179, pp. 2553–2558 (1978).

K. H. Reichert, et al., "Zur Kinetik der Niederdruckpolymerisation . . . ," *Die Makromolekulare Chemie*, vol. 169, pp. 163–176 (1973).

S. Collins, et al., "Polymerization of Propylene Using Supported, Chiral, ansa–Metaallocene Catalysts: Production of Polypropylene with Narrow Molecular Weight Distributions", *Macromolecules*, vol. 25, pp. 1780–1785 (1992).

J. Chien, et al.,: "Olefin Copolymerizatiuon with Metallocene Catalysts. III. Supported Metallocene/Methylaluminoxane Catalyst for Olefin Copolymerization", *Journal of Polymer Science, Part A: Polymer Chemistry*, vol. 29, pp. 1603–1607 (1991).

J. Chien, et al.,: "Olefin Copolymerization with Metallocene Catalysts. IV. Metallocene/Methylaluminoxane Catalyzed Olefin Terpolymerization", *Journal of Polymer Science, Part A: Polymer Chemistry*, vol. 29, pp. 1609–1613 (1991).

*Primary Examiner*—Porfirio Nazario-Gonzalez
*Attorney, Agent, or Firm*—Ladas & Parry

[57] ABSTRACT

Catalyst component for the polymerization of alpha-olefins of general formula (I)

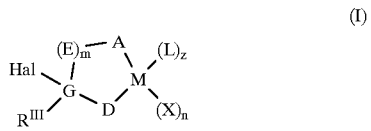

wherein:

M is a transition metal of groups 3, 4–10, lanthanide or actinide of the periodic table of the elements; A is a ring with delocalized $\pi$ electrons, L is a neutral Lewis base; m is an integer whose value can be: 0 or 1; E is selected from the group comprising: $BR''$, $CR''_2$, $SiR''_2$, $GeR''_2$; Hal is selected from the group comprising iodine, bromine or chlorine; $R'''$ has the same meaning of $R''$; Si is a silicon atom; D is selected from the group comprising: O, S, $NR^{IV}$, $PR^{IV}$, $OR^{IV}$, $SR^{IV}$, $NR^{IV}_2$, $PR^{IV}_2$; each X group equal to or different from each other is selected from the group comprising hydrogen, halide, alkyl, cycloalkyl, aryl, alkenyl, arylallyl, arylalkenyl or alkylaryl with 1 to 20 carbon atoms, n is a number whose value can be: 0, 1, 2 or 3, in order to full the remaining valences of metal M. It is also described a method for supporting the compound of formula I.

27 Claims, 1 Drawing Sheet

ORGANOMETALLIC CATALYSTS FOR THE POLYMERIZATION AND COPOLYMERIZATION OF ALPHA-OLEFINS

Incorporated herein by this reference is Spanish Appln. No. 9602302 filed on Oct. 30, 1996. This U.S. application claims priority 35 U.S.C. 119 to Spanish Appln. No. 9602302, filed on Oct. 30, 1996.

BACKGROUND

The present invention relates to a new class of organometallic catalysts, to the process for preparation thereof and their use for the polymerization and copolymerization of ethylene and alpha-olefins in industrial production plants.

In EP 416815 and EP 420436 there is the description of a new type of organometallic catalysts in which a transition metal is coordinated to a cyclopentadienyl ring and a heteroatom. These organometallic compounds, when they are activated with alkylaluminoxanes, are able to produce ethylene polymers with high molecular weight and narrow distribution of molecular weight. They moreover own a great effectiveness in comonomer incorporation. However, when the comonomer content of the polymeric chain is increasing, the molecular weight sensibly decreases (though in these patents there is the description of some synthetic methods to obtain this new type of organometallic complexes, these methods are not useful to prepare the compounds of general formula I).

The use of the catalysts described in patents EP 416815 and EP 420436 is limited to solution processes and mass processes at high temperatures and pressures. The homogeneous catalytic systems have the disadvantage that when they are used in suspension polymerization processes, a part of the produced polymer adheres to the reactor walls: this effect is technically called "reactor fouling". Besides, in most cases, the obtained polymers have a very small particle size and low apparent densities, limiting the industrial production. In order to avoid the reactor from fouling and obtain polymers with high apparent density, the homogeneous systems must be heterogenized on an organic or inorganic support.

Some techniques for heterogenizing organometallic complexes on inorganic supports are based on the simple adsorption of the organometallic compound onto the inorganic support [S. Collins Macromolecules 25, 1780(1992) and J C W Chien J. Polym. Sci., Part A: Polym. Chem. 29, 1603 (1991)]. This process has the disadvantage that the union between the organometallic complex and the inorganic support is not very strong, as there can be loss of the organometallic compound during the polymerization process, causing the fouling of the polymerization reactor. Other processes are based on the modification of the inorganic support with methylaluminoxane before the incorporation of the organometallic complex (EP 668295, WO 9205203, WO 9407928 and WO 9403506), but they have the disadvantage that the obtained solid catalysts must be activated with additional quantities of aluminoxane for its use in polymerization. Besides, the obtained polymers apparent densities are not as good as it would be desirable.

As a consequence, there is the need for heterogenization processes that advantageously exceed those described in patents EP 668295 and WO 9403506. The problem can be solved by the introduction of a reactive halogen in the bridge of the organometallic complex, producing new complexes, that can be advantageously used in order to obtain heterogeneous catalytic systems prepared by a chemical reaction with an organic or inorganic support as described in EP 757992. Besides these catalysts produce polymers with a good apparent densities.

Therefore an object of the present invention is the production of new organometallic complexes whit a reactive halogen in the bridge and their heterogenization on an organic or inorganic support.

Further object of the present invention is a suitable method for the preparation of said complexes. This synthesis method is novel and more suitable than those already known in the art.

DESCRIPTION OF THE INVENTION

The present invention relates to homogeneous and heterogeneous organometallic catalytic systems, which can polymerize and copolymerize ethylene and alpha-olefins, in particular they can homopolymerize ethylene and copolymerize ethylene with alpha-olefins.

The organometallic catalyst of the invention, is defined by the general formula (I):

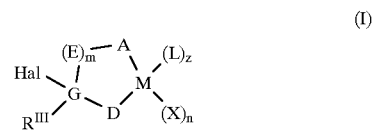

wherein:

M is a transition metal of groups 3, 4–10, lanthanide or actinide of the periodic table of the elements, preferably titanium, zirconium or hafnium.

A is a ring with delocalized $\pi$ electrons, that directly coordinates to the transition metal M; preferably A is a cyclopentadienyl type of ring of formula $C_5R_4$, wherein each R group, equal to or different from each other, is selected from the group comprising: hydrogen, $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, branched or linear, whose hydrogens are optionally substituted by $SiR^I_3$, $GeR^I_3$, $OR^I$, $NR^I_2$, $OSiR^I_3$ groups or any combination thereof wherein $R^I$ is selected from the group comprising: hydrogen, $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, branched or linear. R is also selected from the group comprising $SiR^I_3$, $GeR^I_3$, $OR^I$, $NR^I_2$, $OSiR^I_3$ groups or any combination thereof. Two adjacent R groups optionally unite in order to form a saturated or unsaturated polycyclic cyclopentadienyl ring such as indenyl, tetrahydroindenyl, fluorenyl or octahydrofluorenyl, optionally substituted with R groups.

L is a neutral Lewis base such as diethylether, tetrahydrofurane, dimethylaniline, aniline, triphenylphosphine, n-butylamine, etc.

z is a number whose value is: 0, 1, 2 or 3.

m is an integer whose value is: 0 or 1; preferably m is equal to 0;

E is selected from the group comprising: $BR^{II}$, $CR^{II}_2$, $SiR^{II}_2$, $GeR^{II}_2$. Each $R^{II}$, equal to or different from each other, is hydrogen, halogen, alkyl, cycloalkyl, aryl, alkenyl, arylalkyl, arylalkenyl or alkylaryl with 1 to 20 carbon atoms, linear or branched, whose hydrogens are optionally substituted by $SiR^I_3$, $GeR^I_3$, $OR^I$, $NR^I_2$, $OSiR^I_3$ or any combination thereof wherein $R^I$ is above defined. Besides $R^{II}$ and $R^{III}$ optionally unite to form a ring.

Hal is selected from the group comprising iodine, bromine or chlorine. It is preferably chlorine. $R^{III}$ has the same meaning of $R^{II}$. It is preferably methyl. G is a silicon or a germanium atom.

D is selected from the group comprising: O, S, $NR^{IV}$, $PR^{IV}$ or a neutral ligand which gives two electrons such as: $OR^{IV}$, $SR^{IV}$, $NR^{IV}_2$, $PR^{IV}_2$. Each $R^{IV}$, equal to or different from each other, is hydrogen, alkyl, cycloalkyl, aryl, alkenyl, arylalkyl, arylalkenyl or alkylaryl from 1 to 20 carbon atoms, linear or branched, whose hydrogens are optionally substituted by $SiR^I_3$, $GeR^I_3$, $OR^I$, $NR^I_2$, $OSiR^I_3$ groups or any combination thereof wherein $R^I$ is above defined. $R^{IV}$ optionally forms a condensed cycle through another bond with $R^{II}$ or $R^{III}$. When D is neutral, the bond between M and D is more exactly described as a coordinative-dative bond.

Each X group equal to or different from each other is selected from the group comprising hydrogen, halide, alkyl, cycloalkyl, aryl, alkenyl, arylalkyl, arylalkenyl or alkylaryl with 1 to 20 carbon atoms, linear or branched, whose hydrogens are optionally substituted by $SiR^I_3$, $GeR^I_3$, $OR^I$, $NR^I_2$, $OSiR^I_3$ groups or any combination thereof wherein $R^I$ is above defined.

n is a number whose value is: 0, 1, 2 or 3, in order to fill the remaining valences of metal M.

The organometallic complexes of general formula (I) when D is $NR^{IV}$ and m is equal to 0, can be suitably prepared starting from the substituted monocyclopentadienyl complexes, of formula:

$$X_3M-A-(E)_m-\underset{\underset{Hal}{|}}{\overset{\overset{R^{III}}{|}}{G}}-Hal$$

by reaction with the alkali metal compound $M'NHR^{IV}$ according to the following scheme:

$$X_3M-A-(E)_m-\underset{\underset{Hal}{|}}{\overset{\overset{R^{III}}{|}}{G}}-Hal + M'HNR^{IV} + N(R^V)_3$$

↓

[structure with (E)_m, A, M, X, G, N, Hal, $R^{III}$, $R^{IV}$] X + M'Hal + $XN(R^V)_3H$ Wherein $R^V$ has the same meaning of $R^{IV}$ and M' is selected from the group comprising Li, Na, K.

The compound of general formula:

$$X_3M-A-(E)_m-\underset{\underset{Hal}{|}}{\overset{\overset{R^{III}}{|}}{G}}-Hal$$

can be prepared through the reaction of the transition metal compound of formula $MX_4$, or of certain aducts of formula $MX_4 \cdot 2L$, with the 1-trialkylsilyl-cyclopentadienes of general formula:

$$(R^{VI})_3Si-A-(E)_m-\underset{\underset{Hal}{|}}{\overset{\overset{R^{III}}{|}}{G}}-Hal$$

where $R^{VI}$ is an alkyl group from 1 to 20 carbon atoms, preferably methyl according the following scheme:

$$(R^{VI})_3Si-A-(E)_m-\underset{\underset{Hal}{|}}{\overset{\overset{R^{III}}{|}}{G}}-Hal + MX_4 \longrightarrow$$

$$X_3M-A-(E)_m-\underset{\underset{Hal}{|}}{\overset{\overset{R^{III}}{|}}{G}}-Hal + (R^{VI})_3Si-X$$

Finally, the ligands of general formula:

$$(R^{VI})_3Si-A-(E)_m-\underset{\underset{Hal}{|}}{\overset{\overset{R^{III}}{|}}{G}}-Hal$$

can be synthesized from available commercial products.

During the process, the reaction temperature is maintained between −100° C. and 95° C., preferably between −80° C. and 80° C., preferably realizing the operations in nitrogen inert atmosphere.

As non polar solvents, pentane, hexane and toluene can be used; as polar aprotic solvents ethers such as diethyl ether, tetrahydrofurane or dimethoxyethane can be used.

During the whole process, both the chemical species and the solvents were protected from oxygen and humidity. The organometallic catalysts when stored in inert atmosphere, remain active for long periods of time.

Non-limiting examples of compounds of general formula (I) according to the present invention, are:
(tertbutylamide chloro cyclopentadienyl-methylsilanediyl) titanium dichloride
(tertbutylamide chloro cyclopentadienyl-methylsilanediyl)) zirconium dichloride
(tertbutylamide chloro cyclopentadienyl-methylsilanediyl)) hafnium dichloride
(tertbutylamide chloro 1-indenyl methylsilanediyl)-titanium dichloride
(tertbutylamide chloro 1-indenyl methylsilanediyl)-zirconium dichloride
(tertbutylamide chloro 1-indenyl methylsilanediyl)-hafnium dichloride
(tertbutylamide chloro 1-(2-methylindenyl) methylsilanediyl)titanium dichloride
(tertbutylamide chloro 1-(2-methylindenyl) methylsilanediyl)zirconium dichloride
(tertbutylamide chloro 1-(2-methylindenyl) methylsilanediyl)hafnium dichloride The organometallic catalysts, obtained as it has been previously described, can be used in the polymerization and copolymerization of alpha-olefins through the addition of cocatalysts. These cocatalysts are compounds which can form non-coordinative anions, such as alkylaluminoxanes or boron perfluorinated compounds. Representative, but non-limiting, examples are methylaluminoxane, ethylaluminoxane, N,N-dimethylaniliniumtetrakys (pentafluorophenyl)borate, and trispentafluorophenylborane. In case boron derivatives are used, it is preferable to add to the polymerization medium little quantities of aluminium alkyls (TIBA, TEA, TMA, etc.).

The organometallic catalysts, obtained as it has been previously described, can be heterogenised onto organic or inorganic porous supports containing hydroxyl groups, chemically modified or not.

The organic supports useful for the present invention are: styrene-divinylbenzene copolymers, polyols, partially hydrolyzed ethylene-vinylacetate copolymers, etc. These supports can be modified in such a way that they contain hydroxyl groups as well known in the art and for example described in EP 633272.

Non limiting examples of inorganic porous supports containing hydroxyl groups useful for the present invention are oxides, silicates, carbonates, phosphates, clays and mixtures thereof. Some inorganic supports preferably used are silica, alumina, silica-alumina, silica-titanates, silica-vanadates, silica-chromates, aluminium phosphates, phosphatized silica and mixtures thereof. The surface area varies between 10–1000 m$^2$/g, preferably between 150–650 m$^2$/g, the pore volume varies between 0.2–4.0 cm$^3$/g, preferably 0.6–2.7 cm$^3$/g and the average particle size varies between 1–1000 $\mu$m, preferably between 5–100 $\mu$m.

The water contained in the supports can be eliminated or not before the reaction with the organometallic complex that contains active functional groups. In case of inorganic supports, when dehydrated supports are used, they are dried through calcination under inert atmosphere in an oven at temperatures that vary between 120° C. and 1000° C. (typically between 200–800° C.). The hydroxyl groups present in the support can be determined by titration with n-butyl magnesium chloride or with triethylaluminum. The concentration of hydroxyl groups (OH), that depends on the drying temperature, varies between 0.1 and 5 mmol OH/g silica, preferably 0.3 to 3 mmol OH/g silica or between 0.1 and 7 OH groups /nm$^2$, preferably between 0.5 and 5 OH groups /nm$^2$.

Once the drying process has been realized, the support can be stored under inert atmosphere (N$_2$ or Ar), protecting it from air and humidity.

The supports, partially dehydrated or not, can be directly treated with organometallic catalysts, or they can previously be chemically modified through reaction of the hydroxyl groups with compounds of general formula II:

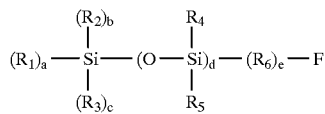
(II)

wherein:
R$_1$ is a group reactive towards the hydroxyl groups of the support. It is selected from the group comprising halogen, alcoxy of formula OR$_7$, R$_7$ being a branched or linear alkyl, with 1 to 6 carbon atoms, C$_5$–C$_7$ cycloalkyl, C$_6$–C$_{10}$ aryl, C$_2$–C$_{10}$ alkenyl, C$_7$–C$_{10}$ arylalkyl or C$_7$–C$_{40}$ alkylaryl.

R$_2$, R$_3$, R$_4$ and R$_5$ equal to or different from each other, are alkyl groups, branched or linear, with 1 to 6 carbon atoms, C$_5$–C$_7$ cycloalkyls, C$_6$–C$_{10}$ aryls, C$_2$–C$_{10}$ alkenyls, C$_7$–C$_{10}$ arylalkyls or C$_7$–C$_{40}$ alkylaryls.

R$_6$ is a propanediyl or methylene group.

F is selected from the group comprising: NH$_2$, NHR$_7$, SH, OH or PHR$_7$, where R$_7$ has already been defined.

The sum a+b+c is 3, a being always higher than 0.

d and e take without distinction values between 0 and 10. Preferably d and e are not at the same time equal to 0.

Representative, but non limiting, examples of some compounds of general formula II, which can serve to functionalize the catalytic supports with terminal amine or tiol groups are: 3-trimetoxysilylpropanetiol, 3-trimetoxysilylpropylamine, N-phenyl-3-trimetoxysilylpropylamine, N-methyl-3-trimetoxysilylpropylamine.

The chemical modification of the support is realized through reaction between superficial hydroxyl groups of the supports and the reactive groups (R$_1$) of the compounds of formula II; the molar ratio OH/R$_1$ is comprised between 0.10 and 6, preferably between 0.2 and 4. The reaction is carried out in hydrocarbon solvents (toluene, heptane, etc.), maintaining the temperature of the reaction medium between 25° C. and 150° C., preferably working between 50 and 130° C., for 5–36 hours, preferably for 10–30 hours. The reaction by-products, generally inert, can be easily eliminated by filtration and washing with hydrocarbon solvents.

Another type of chemical modification of the support, partially dehydrated or not, is by its treatment with organoaluminum compounds such as aluminium alkyl or alkylaluminoxane. Preferably, the alkylaluminoxane is methylaluminoxane, ethylaluminoxane, isobutylaluminoxane.

The quantity of the used organoaluminum compound can vary from 0.05 to 30 mmol of Al per gram of support; however, this quantity can be smaller or larger, the concentration preferably ranges from 1 to 15 mmol Al/g of support. The reaction is completed in 1–24 hours, preferably between 2 and 15 hours, in a temperature range comprised between 15 and 200° C., preferably between 20 and 150° C. The solids obtained through this process have aluminium contents between 2 and 20%, preferably between 5 and 15%.

The anchorage of the organometallic catalyst on the support, chemically modified or not, can be realized through the reaction, under inert atmosphere, of the support with the organometallic catalyst in a hydrocarbon medium (toluene, heptane) from room temperature to reflux temperature of the solvent, for a time comprised between 30 min and 24 h, leaving the formed gas in evolution. Once the reaction is completed, the reaction mixture is filtered and washed with a hydrocarbon solvent several times up to the elimination of the acid remnants or the non-supported catalyst. It is dried under vacuum and stored under inert atmosphere, and it is active for long periods of time.

The quantity of the organometallic complex of general formula I, added to the support, chemically modified or not, can vary between 0.001 and 10 mmol of metal per gram of support, preferably between 0.01 and 7 mmol of metal per gram of support.

The anchorage of the organometallic catalyst to the support through chemical reaction allows to preserve the organometallic compound structure, producing species which are active in the polymerization of olefins in the presence of aluminium and/or boron cocatalysts.

The catalytic systems thus prepared are fit for the polymerization of alpha-olefins with 2 to 20 carbon atoms, in particular for the polymerization of ethylene, and for the copolymerization of ethylene with at least one alpha-olefin with 3 to 20 carbon atoms, such as propylene, 1-butene, 4methyl-1-pentene, 1-hexene, etc., with dienes, with cycloalkenes and with styrene. The polymerization can be realized through a processes in solution, in suspension, in gas phase or in bulk at high pressure and temperature. When using a suspension process, hydrocarbon solvents, such as branched or linear aliphatic hydrocarbons (hexane, heptane, isobutane, etc.), cyclic hydrocarbons (benzene, toluene, xylene, etc.) or a mixture thereof are used as reaction medium. The polymerization can be realized between 1 and 4000 atmospheres and temperatures between 60 and 300° C., preferably between 40 and 220° C., and the polymerization time can vary between 20 seconds and 6 hours, according to the process.

The used concentration of the organometallic catalyst is from $10^{-7}$ to $10^{-3}$ M, preferably form $10^{-6}$ to $10^{-4}$ M. The organo aluminum compound (for example an aluminoxane) is used in a concentration from $10^{-4}$ to $10^{-1}$ M, preferably from $10^{-3}$ to $10^{-2}$ M. However, bigger concentrations of both components are possible as well. When an aluminoxane is used as a cocatalyst, the used Al/M molar ratio ranges from 100 to 10000, preferably between 500 and 1500. When a boron compound is used, the molar ratio varies in the range 0.5–10, preferably 0.9–5.

The molecular weight of the obtained polymers can be controlled by varying the concentrations of catalyst, cocatalyst and monomer in the polymerization medium, the polymerization temperature as well as by the addition of regulators of the molecular weight such as $H_2$. When in the preparation of the catalyst only one type of cocatalyst is used, polymers with narrow distribution of the molecular weight are obtained. However, when several types of catalysts and/or cocatalysts are used, the obtained polymers have broad distribution of the molecular weight, including also multimodal distributions.

The copolymerization reactions can be realized by using the same process as the one used in the homopolymerization processes, but moreover by feeding the reaction medium with the suitable comonomer or comonomers. The preferred comonomer/monomer molar ratio is comprised between 0.1/1 and 5/1. In this way, copolymers with controlled content and random distribution of comonomer are obtained.

FIG. 1 shows some non limiting examples of compounds of formula I.

The following examples are described in order to better understand the invention. The materials, the chemical compounds and the conditions used in these examples are illustrative and do not limit the scope of the invention.

The average molecular weights in number, weight and distribution were determined through gel permeation chromatography GPC or SEC. The intrinsic viscosities [$\mu$] were obtained at 145° C. through viscosimetric techniques, using as a solvent trichlorobenzene with 0.05% of antioxidant in order to prevent polymer degradation.

EXAMPLE I a) Preparation of 1-(Dichloromethylsilyl)-1-(Trimethylsilyl)Cyclopentadiene To a suspension of 12.5 g (87 mmol) of lithium (trimethylsilyl)cyclopentadienide in hexane, 13 g (87 mmol) of methyltrichlorosilane is added at –20° C. One hour later, room temperature is achieved and the compound is stirred for two days. The solution is filtered and concentrated, obtaining a pale yellow liquid corresponding to 1-(dichloromethylsilyl)-1-(trimethylsilyl)cyclopentadiene (13.4 g, 53.3 mmol, yield: 61%). $^1$H-NMR ($C_6D_6$): 6.60(m, 2H), 6.42(m,2H), 0.13(s,3H), 0.04(s,9H).

b) Preparation of [(1-Dichloromethylsilyl) Cyclopentadienyl]Titanium Trichloride To a solution of 2.3 g (12.1 mmol) of titanium tetrachloride in dichlomethane, 3 g (12.1 mmol) of 1-dichloromethylsilyl-1-trimethylsilyl cyclopentadiene is added dropwise at 25° C. The reaction is stirred for two days at room temperature. The solvent is evaporated to dryness and the residue is extracted with hexane. When the hexane solution is concentrated, a yellow solid corresponding to (1-dichloromethylsilyl cyclopentadienyl) titanium trichloride is obtained (2 g, 6 mmol, yield: 50%). $^1$H-NMR ($C_6D_6$): 6.47 (m,2H), 5.49(m,2H), 0.70(s,3H).

c) Preparation of [Tertbutylamide-Chloro-Cyclopentadienylmethylsilaneodiyl Titanium Dichloride To a solution of 2 g (6 mmol) of [(1-dichloromethylsilyl) cyclopentadienyl]titanium trichloride in hexane, 0.47 g (6 mmol) of lithium tertbutylamide and 0.6 g (6 mmol) of triethylamine previously mixed in hexane are added dropwise at –30° C. When the addition is completed, the stirring is maintained for 16 hours. The reaction mixture is filtered and the resulting solution is brought to dryness, obtaining an orange solid (0.8 g, 2.4 mmol, yield: 40%). $^1$H-NMR ($C_6D_6$): 6.31(m,2H), 5.81(m,2H), 1.44(s,9H), 0.42(s,3H).

EXAMPLE 2

In a glass reactor of the capacity of 250 ml, equipped with mechanic stirrer and introduced in a thermostatic bath, we added 0.85 g. of silica previously calcinated at 400° C. for 6 hours in a fluidized bed calcination oven under inert atmosphere. Afterwards, 50 ml. of toluene previously dried on metallic sodium was added. On this suspension a solution of 140 mg of [$\eta^5(C_5H_4)$BuN-SiMeCl]TiCl$_2$ in toluene was added under inert atmosphere. It was warmed up to 40° C. and the stirring was maintained for 4 hours. The solid was filtered, washed several times (5×100 ml) with dry toluene and it was then dried at reduced pressure for 12 hours. The red final solid contained 2.2% by weight of Ti. This catalyst is stable under nitrogen for long periods of time.

EXAMPLE 3

In a glass reactor of the capacity of 250 ml, equipped with mechanic stirrer and introduced in a thermostatic bath, we added 1.1 g of silica previously calcined at 800° C. for 6 hours in a fluidified bed calcination oven under inert atmosphere. Afterwards, 50 ml of toluene previously dried on metallic sodium are added. On this suspension a solution of 284 mg of [tBuN-SiMeCl-Cp]TiCl$_2$ in toluene was added in inert atmosphere. It was warmed at 40° C. and the stirring was maintained for 24 hours. The solid was filtered, washed several times (5×100 ml) with dry toluene and it is then dried at reduced pressure for 12 hours. The red final solid contains 1.98% by weight of Ti. This catalyst is stable under nitrogen for long periods of time.

EXAMPLE 4

To a glass reactor of 1 liter, previously dried and degassed, 600 ml of n-heptane was added. The temperature was raised to 70° C. and the solvent was stirred at 1200 rpm. When the thermic equilibrium was achieved, the medium was saturated with ethylene at a pressure of 4 bar. 3.3 ml. of a MAO solution in toluene (1.5 M in total aluminium) at 2 bar of ethylene pressure was added. The pressure was raised to 4 bar and 2 minutes later we added 0.01 mmol of the organometallic compound described in example 1 mixed in toluene, followed by the immediate addition of 0.01 mmol of N,N-dimethylanyliniumtetrakys(pentafluorophenyl) borate mixed in toluene. The system was fed with ethylene for 15 minutes and then the polymerization was stopped by closing the ethylene flux and adding 20 ml of acidified methanol. 1 g of a polyethylene with an Mw of 337220 and a Mw/Mn of 7.2 with a bimodal character was obtained.

EXAMPLE 5

Ethylene was polymerized in the same way as in example 4, but using 20 ml of a MAO solution in toluene (1.5 M in total aluminium) and 22 mg of the solid catalyst described in example 2. After 15 minutes of polymerization 1.54 g of polyethylene with an Mw of 281,604 and an Mw/Mn of 3.5 was obtained.

EXAMPLE 6

Ethylene and 1-hexene were copolymerized. The same method as example 4 was used, but once the solvent had been added and before the reactor was pressurized, 8 ml of dry and just distilled 1-hexene were injected. 20 ml of a MAO solution in toluene (1.5 M in total aluminium) and 22 mg of the solid catalyst described in example 2 were used. After 15 minutes of polymerization 1 g. of polyethylene with an Mw of 271244 and an Mw/Mn of 3.6 was obtained. The content in 1-hexene determined by $^{13}$C-NMR was 0.5% molar, distributed at random.

EXAMPLE 7

To a glass reactor of 1 liter, previously dried and degassed, 600 ml of n-heptane was added. The temperature was raised to 70° C. and the solvent was stirred at 1200 rpm. When the thermic equilibrium was achieved, the medium was saturated with ethylene at a pressure of 4 bar. 10 ml of a MAO solution in toluene (1.5 M in total aluminum) at 2 bar of ethylene was added. The pressure was raised to 4 bar and 2 minutes later we added 0.01 mmol of the organometallic compound described in example 3 mixed in toluene. The system was fed with ethylene for 15 minutes and then the polymerization was stopped by closing the ethylene flux and adding 20 ml of acidified methanol. 1.2 g of a polyethylene with an Mw of 531,376 was obtained.

EXAMPLE 8

Ethylene and 1-hexene were copolymerized. The same method as example 7 was used, but once the solvent had been added and before the reactor was pressurized, 8 ml of dry and just distilled 1-hexene were injected. After 15 minutes of polymerization 0.7 g of polyethylene with an Mw of 235,486 was obtained. The content in 1-hexene determined by $^{13}$C-NMR was 0.91% molar, distributed at random.

EXAMPLE 9

Ethylene and 1-hexene were copolymerized. The same method as example 7 was used, but once the solvent had been added and before the reactor was pressurized, 16 ml of dry and just distilled 1-hexene were injected. After 15 minutes of polymerization 0.3 g of polyethylene with an Mw of 175641 was obtained. The content in 1-hexene determined by $^{13}$C-NMR was 1.06% molar, distributed at random.

EXAMPLE 10

Ethylene was polymerized in the same way as example 7, but using 20 ml of a MAO solution in toluene (1.5 M in total aluminum) and 65 mg of the solid catalyst described in example 2. After 15 minutes of polymerization 1.59 g of polyethylene with an Mw of 250,268 and an Mw/Mn of 3.0 was obtained.

EXAMPLE 11

Ethylene and 1-hexene were copolymerized. The same method as example 10 was used, but once the solvent had been added and before the reactor was pressurized, 4 ml of dry and just distilled 1-hexene were injected. After 15 minutes of polymerization 5.3 g of polyethylene with an Mw of 150030 and Mw/Mn=2.1 was obtained. The content in 1-hexene determined by $^{13}$C-NMR was 0.27% molar, distributed at random.

EXAMPLE 12

Ethylene and 1-hexene were copolymerized. The same method as example 10 was used, but once the solvent had been added and before the reactor was pressurized, 16 ml of dry and just distilled 1-hexene were injected. After 15 minutes of polymerization 0.56 g of polyethylene with an Mw of 232,679 and Mw/Mn=3.9 was obtained. The molar content in 1-hexene determined by $^{13}$C-NMR was 0.56% distributed at random.

EXAMPLE 13

Ethylene was polymerized in the same way as example 7, but using 20 ml of a MAO solution in toluene (1.5 in total aluminum) and 73 mg of the solid catalyst described above. After 15 minutes of polymerization 1.70 g of polyethylene with an Mw of 207,722 and an Mw/Mn of 2.9 was obtained.

EXAMPLE 14

Ethylene and 1-hexene were copolymerized. The same method as example 13 was used, but once the solvent had been added and before the reactor was pressurized, 8 ml of dry and just distilled 1-hexene were injected. After 15 minutes of polymerization 1.27 g of polyethylene with an Mw of 239,282 was obtained. The molar content in 1-hexene determined by $^{13}$C-NMR was 0.57% distributed at random.

EXAMPLE 15

Ethylene and 1-hexene were copolymerized. The same method as example 13 was used, but once the solvent had been added and before the reactor was pressurized 4 ml of dry and just distilled 1-hexene were injected. After 15 minutes of polymerization 0.47 g of polyethylene with an Mw of 326,694 was obtained. The molar content in 1-hexene determined by $^{13}$C-NMR was 0.042% distributed at random.

We claim:

1. Catalyst component for the polymerisation of alpha-olefins of general formula (I):

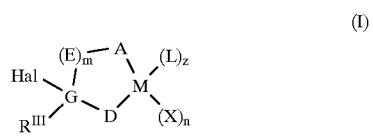

wherein:

M is a transition metal of groups 3, 4–10, lanthanide or actinide series of the periodic table of the elements;

A is a ring with delocalized π electrons, that directly coordinates to the transition metal M;

L is a neutral Lewis base;

z is a number whose value is: 0, 1, 2 or 3;

m is an integer whose value is: 0 or 1;

E is selected from the group consisting of: $BR''_2$, $CR''_2$, $SiR''_2$, $GeR''_2$; each $R''$, equal to or different from each other, is hydrogen, halogen, alkyl, cycloalkyl, aryl, alkenyl, arylalkyl, arylalkenyl and alkylaryl with 1 to 20 carbon atoms, linear or branched, which hydrogen are optionally substituted by $SiR'_3$, $GeR'_3$, $OR'$, $NR'_2$, $OSiR'_3$ groups or any combination thereof, wherein $R'$ is selected from the group consisting of: hydrogen, $C_1-C_{20}$ alkyl, $C_3-C_{20}$ cycloalkyl, $C_6-C_{20}$ aryl, $C_7-C_{20}$ alkenyl, $C_7-C_{20}$ arylalkyl, $C_7-C_{20}$ arylalkenyl and alkylaryl, branched or linear; besides $R''$ and $R'''$ optionally form a ring;

Hal is selected from the group consisting of iodine, bromine and chlorine;

$R'''$ has the same meaning of $R''$; G is a silicon or a germanium atom;

D is selected from the group consisting of: O, S, $NR^{IV}$, $PR^{IV}$, $OR^{IV}$, $SR^{IV}$, $NR^{IV}_2$ and $PR^{IV}_2$; each $R^{IV}$, equal to or different from each other, is hydrogen, alkyl, cycloalkyl, aryl, alkenyl, arylalkyl, arylalkenyl or alkylaryl from 1 to 20 carbon atoms, linear or branched, whose hydrogens are optionally substituted by $SiR'_3$, $GeR'_3$, $OR'$, $NR'_2$, $OSiR'_3$ groups or any combination thereof wherein $R'$ is above defined; it optionally forms a condensed ring through another bond with $R''$ or $R'''$;

each X group equal to or different from each other is selected from the group consisting of hydrogen, halide, alkyl, cycloalkyl, aryl, alkenyl, arylalkyl, arylalkenyl and alkylaryl with 1 to 20 carbon atoms, linear or branched, where hydrogens are optionally substituted by $SiR'_3$, $GeR'_3$, $OR'$, $NR'_2$, $OSiR'_3$ groups or any combination thereof wherein $R'$ is above defined;

n is a number whose value is: 0, 1, 2 or 3, in order to fill the remaining valences of metal M.

2. Catalyst component according to claim 1, wherein the general formula (I) A is a cyclopentadienyl type of ring of formula $C_5R_4$, wherein each R group, equal to or different from each other, is selected from the group consisting of: hydrogen $C_1-C_{20}$ alkyl, $C_3-C_{20}$ cycloalkyl, $C_6-C_{20}$ aryl, $C_7-C_{20}$ alkenyl, $C_7-C_{20}$ arylalkyl, $C_7-C_{20}$ arylalkenyl and alkylaryl, branched or linear, the hydrogens of these groups are optionally substituted by $SiR'_3$, $GeR'_3$, $R'O$, $R'_2N$, $OSiR'_3$ groups or any combination thereof wherein $R'$ is selected from the group consisting of: hydrogen, $C_1-C_{20}$ alkyl, $C_3-C_{20}$ cycloalkyl, $C_6-C_{20}$ aryl, $C_7-C_{20}$ alkenyl, $C_7-C_{20}$ arylalkyl, $C_7-C_{20}$ arylalkenyl and alkylaryl, branched or linear; R is also selected from the group consisting of $SiR'_3$, $GeR'_3$, $OR'$, $NR'_2$ and $OSiR'_3$ groups or any combination thereof; two adjacent R optionally unite in order to form a saturated or unsaturated polycyclic cyclopentadienyl ring.

3. Catalyst component as claimed in claim 2, wherein the saturated or unsaturated polycyclic cyclopentadienyl ring is selected from the group consisting of indenyl, tetrahydroindenyl, fluorenyl and octahydrofluorenyl, optionally substituted with R groups.

4. Catalyst component according to claim 1, wherein the general formula (I) M is selected from the group consisting of: zirconium, titanium and hafnium.

5. Catalyst component according to claim 1, wherein Hal is chlorine.

6. Catalyst component according to claim 1, wherein $R'''$ is methyl.

7. Solid catalyst component obtainable by contacting a catalyst component of claim 1 and an organic support or inorganic support with functional hydroxyl groups.

8. Solid catalyst component according to claim 7 wherein the support is selected from the group consisting of: styrene-divinylbenzene copolymers, polyols, partially hydrolyzed ethylene-vinylacetate copolymers, silica, alumina, silica-alumina, silica-titanates, silica-vanadates, silica-chromates, aluminium phosphates, phosphatized silica and mixtures thereof.

9. Solid catalyst component according to claim 7 wherein the organic or inorganic support is previously modified through reaction with compounds of general formula (II):

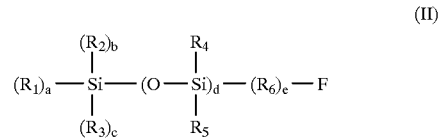

wherein:

$R_1$ is a group reactive towards the hydroxyl groups of the support selected from the group consisting of: halogen, alkoxy of formula $OR_7$, $R_7$ being a branched or linear alkyl, with 1 to 6 carbon atoms, a $C_5-C_7$ cycloalkyl, a $C_6-C_{10}$ aryl, a $C_2-C_{10}$ alkenyl, a $C_7-C_{10}$ arylalkyl or $C_7-C_{40}$ alkylaryl;

$R_2$, $R_3$, $R_4$ and $R_5$, equal to or different from each other, are alkyl groups, branched or not, with 1 to 6 carbon atoms, $C_5-C_7$ cycloalkyl, $C_6-C_{10}$ aryl, $C_2-C_{10}$ alkenyl, $C_7-C_{10}$ arylalkyl or $C_7-C_{40}$ alkylaryl;

$R_6$ is a propanediyl or methylene group;

F is selected from the group consisting of: $NH_2$, $NHR_7$, SH, OH and $PHR_7$, where $R_7$ has already been defined;

the sum a+b+c is 3, a being always higher than 0; and d and e take independently values between 0 and 10.

10. Solid catalyst component according to claim 9 wherein the molar ratio between the superficial hydroxyl group of the support and the reactive groups, $R_1$, is comprised between 0.10 and 6.

11. Solid catalyst component according to claim 10 wherein the molar ratio between the superficial hydroxyl group of the support and the reactive groups, $R_1$, is comprised between 0.2 and 4.

12. Solid catalyst component according to claim 7 wherein the organic or inorganic support, is previously treated with an organo-aluminium compound selected from the group consisting of: aluminium alkyl and alkylaluminoxane.

13. Solid catalyst component according to claim 12 wherein the organo-aluminium compound are selected from the group consisting of trimethylaluminium, triethylaluminium, triisobutylaluminium, methylaluminoxane, ethylaluminoxane and isobutylaluminoxane.

14. Solid catalyst component according to claim 7, wherein the support, has a surface area that varies between 10–1000 $m^2/g$, the pore volume varies between 0.2–4 $cm^3/g$ and the particle medium size varies between 1–500 $\mu$m.

15. Solid catalyst component according to claim 7 wherein the ratio between millimoles of the transition metal and gram of support is comprised between 0.001 and 10.

16. Solid catalyst component according to claim 15 wherein the ratio between millimoles of the transition metal and gram of support, is comprised between 0.01 and 7.

17. Catalyst system comprising:

a cocatalyst selected from the group consisting of: alkylaluminoxane and modified aluminoxane, boron compounds; and a catalyst component according to claim 1.

18. Catalyst system according to claim 17 wherein the cocatalyst is selected from the group consisting of: methylaluminoxane, ethylaluminoxane, N,N-dimethylaniliniumtetrakys (pentafluorophenyl)borate, and trispentafluorophenylborane.

19. Process for obtaining polyolefins in solution, in suspension, in gas phase at low and high pressures and temperatures or in mass at high pressures and high or low temperatures, wherein the catalytic system according to claim 17 is used.

20. Process for obtaining polyolefins according to claim 19, wherein the polymerization temperature varies between −60° C. and 300° C., the pressure varies between 1 and 4000 atmospheres, the transition metal concentration varies between $10^{-7}$ and $10^{-3}$ M, the cocatalyst is an aluminium organocomplex and the cocatalyst/transition metal molar ratio varies between 10 and 10000.

21. Process for obtaining polyolefins according to claim 19, wherein the polymerization temperature varies between −60° C. and 300° C., the pressure varies between 1 and 4000 atmospheres, the transition metal molar concentration varies between $10^{-7}$ and $10^{-3}$, the cocatalyst is a boron compound and the cocatalyst/transition metal molar ratio varies between 0.5 and 10.

22. Process for obtaining polyolefins according to claim 21, wherein the polymerization temperature varies between 40° C. and 220° C., the pressure varies between 1 and 4000 atmospheres, the transition metal molar concentration varies between $10^{-6}$ and $10^{-4}$, the cocatalyst is a boron compound and the cocatalyst/transition metal molar ratio varies between 0.9 and 5.

23. Process for obtaining polyolefins according to claim 20, wherein the polymerization temperature varies between −40° C. and 220° C., the pressure varies between 1 and 4000 atmospheres, the transition metal concentration varies between $10^{-6}$ and $10^{-4}$ M, the cocatalyst is an aluminium organocomplex and the cocatalyst/transition metal molar ratio varies between 500 and 1500.

24. Process for obtaining polyolefins according to claim 19, wherein the monomer is ethylene.

25. Process for obtaining ethylene copolymers according to claim 24, wherein the comonomer is selected from the group consisting of: propene, 1-butene, 1-hexene, 1-octene, 1-hexadecene, 4-methyl-pentene, hexadiene and styrene and mixtures thereof.

26. Process for obtaining a catalyst component according to claim 1 comprising the following steps:

a) reaction of a compound of general formula:

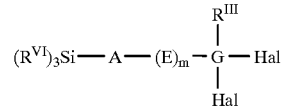

with a compound of a transition metal $MX_4$;

b) reaction of the compound obtained

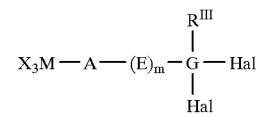

with the alkali metal compound of formula $M'NHR^{IV}$ according to the following scheme:

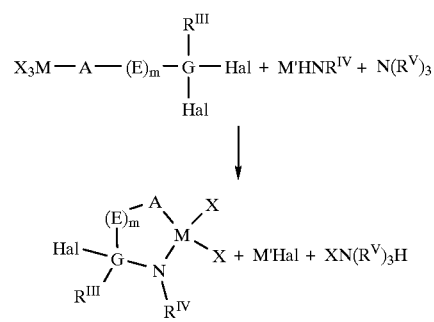

wherein $R^V$ has the same meaning of $R^{IV}$; $R^{VI}$ is an alkyl group from 1 to 20 carbon atoms, M' is selected from the group consisting of Li, K and Na.

27. Process for obtaining a catalyst component according to claim 26 wherein $R^{VI}$ is methyl, and Hal is chlorine.

* * * * *

UNITED STATES PATENT AND TRADEMARK OFFICE
CERTIFICATE OF CORRECTION

PATENT NO. : 5,977,392
DATED : November 2, 1999
INVENTOR(S) : Royo et al.

It is certified that error appears in the above-identified patent and that said Letters Patent is hereby corrected as shown below:

Claim 2, line 17, after "ring" and before the period insert --optionally substituted with R groups--.

Claim 3, lines 4-5, delete "optionally substituted with R groups".

Claim 25, line 4, delete "and styrene" and substitute therefor --, styrene--.

Signed and Sealed this

Eighteenth Day of July, 2000

Q. TODD DICKINSON

Attest:

Attesting Officer

Director of Patents and Trademarks